United States Patent [19]

Stahl

[11] Patent Number: 4,806,478

[45] Date of Patent: Feb. 21, 1989

[54] DRY ENZYME FORMULATIONS CONTAINING D-AMINO ACID OXIDASE

[75] Inventor: Julie B. Stahl, St. Paul, Minn.

[73] Assignee: Minnesota Mining and Manufacturing Company, St. Paul, Minn.

[21] Appl. No.: 661,662

[22] Filed: Oct. 17, 1984

[51] Int. Cl.$^4$ .................. C12N 11/08; C12N 9/96; C12Q 1/26

[52] U.S. Cl. .................. 435/180; 435/25; 435/188; 435/189

[58] Field of Search .................. 435/18, 23–25, 435/28, 29, 32, 180, 188, 189, 805, 810; 422/55, 56, 74

[56] References Cited

U.S. PATENT DOCUMENTS

| | | | |
|---|---|---|---|
| 3,802,842 | 4/1974 | Lange | 23/253 TP |
| 3,897,214 | 7/1975 | Lange et al. | 435/805 X |
| 3,978,185 | 8/1976 | Buntin et al. | 264/518 |
| 4,046,514 | 9/1977 | Johnston | 23/253 TP |
| 4,390,621 | 6/1977 | Bauer | 435/14 |
| 4,391,905 | 7/1983 | Bauer | 435/25 X |
| 4,427,632 | 1/1984 | Okaniwa et al. | 435/14 X |
| 4,442,204 | 4/1984 | Greenquist et al. | 436/518 |
| 4,546,076 | 10/1985 | Degelaen et al. | 435/188 X |
| 4,555,484 | 11/1985 | LaRossa et al. | 435/805 X |

FOREIGN PATENT DOCUMENTS 0101945  3/1984  European Pat. Off. .
2087074  5/1982  United Kingdom .

OTHER PUBLICATIONS

*Chemical Abstracts*, vol. 83, No. 17, 1975, p. 199, Abstract No. 143667x, Kawashima, K. et al.

Frere, J. et al, "Enzymatic Method for Rapid and Sensitive Determination of Beta-Lactum Antibiotics' Antimicrobial Agents and Chemotherapy", Oct. 1980, vol. 18, No. 4, pp. 506–510.

Carrea, G. et al, *Biochim. Biophys. Acta*, vol. 745, 1983, pp. 181–188.

*Primary Examiner*—Charles F. Warren
*Assistant Examiner*—Jeremy M. Jay
*Attorney, Agent, or Firm*—Donald M. Sell; Philip M. Goldman

[57] ABSTRACT

A stable formulation of a non-cellulosic fabric having D-amino acid oxidase coated and dried thereon is shown. The fabric may be woven, nonwoven, or knit and may be made from polyolefin, nylon, polyester, or polyurethane fabrics. Polyolefin fabrics may be pretreated with a surfactant. Also shown are formulations containing some or all of the reagents used to detect beta lactam antibiotics. Kits having webs coated with analytically effective amounts of D-amino acid oxidase, peroxidase, flavin adenine, dinucleotide, a peroxide sensitive dye and a D,D-carboxypeptidase substrate containing a carboxyterminal D-alanine are shown. D,D-carboxypeptidase R39 enzyme may be provided separately in either aqueous form or dried on a separate piece of fabric. Under appropriate conditions the D,D-carboxypeptidase may also be dried on the fabric.

9 Claims, No Drawings

DRY ENZYME FORMULATIONS CONTAINING D-AMINO ACID OXIDASE

FIELD OF THE INVENTION

This invention relates to an improved enzymatic assay. More particularly, the invention relates to improved assays containing the enzyme D-amino acid oxidase wherein the enzyme can be dried and stored for extended periods.

BACKGROUND OF THE INVENTION

The enzyme D-amino acid oxidase is known to be useful in tests to detect the presence of D-alanine. One such assay of particular commercial importance is used to detect the presence of beta-lactam antibiotics in milk. Assays for beta-lactam antibiotics (e.g., penicillins and cephalosporins) are important because large quantities of milk must be discarded each year due to antibiotic contamination.

Frere et al ("Enzymatic Method for Rapid and Sensitive Determination of beta-lactam Antibiotics" Antimicrobial Agents and Chemotherapy, Oct. 1980 pp. 506–510) describe an enzymatic assay for beta-lactam antibiotics using D-amino acid oxidase as part of a reagent system which produces a color change in the presence of D-alanine. That assay relies on the ability of beta-lactam antibiotics to inactivate a specific D,D-carboxypeptidase produced by Actinomadura R39. Other streptomyces D,D-carboxypeptidases are known to be reversably inhibited by beta-lactam antibiotics, but the R39 enzyme is preferred because the rate of inactivation is very rapid and the reversal of inhibition is very slow.

The assay as described by Frere et al is similar to a commercial test known as "Penzym" ® sold by UCB Bioproducts, Brussels, Belgium. The Penzym ® system is sold in seven vials and involves seven steps which take an extended period (20 to 30 minutes).

In the first step D,D-carboxypeptidase is added to the sample and incubated for a period of time, e.g., five minutes. If the sample contains beta-lactam antibiotic, the enzyme will be inactivated to a degree depending on the amount of antibiotic present. Next a substrate for D,D-carboxypeptidase which is a peptide containing a carboxyterminal D-alanine is added.

After further incubation (e.g., 15 minutes), other reagents are added to detect liberation of D-alanine from the substrate. These reagents include D-amino acid oxidase, its co-factor flavin adenine dinucleotide, a peroxide sensitive dye and peroxidase to catalyze the color forming reaction. D-amino acid oxidase oxidizes the D-alanine into pyruvic acid with simultaneous formation of hydrogen peroxide. The hydrogen peroxide oxidizes an organic redox indicator, e.g, o-dianisidine, which produces a distinctive color. At the end of the incubation period a strong acid is added to terminate the reaction and stabilize the color formation.

The Penzym ® kit is supplied with seven separate reagents including: (1) the D,D-carboxypeptidase; (2) a buffer for the D,D-carboxypeptidase; (3) substrate for the D,D-carboxypeptidase, N,N,Diacetyl-2-L-lysyl-D-alanyl-D-alanine: (4) flavin adenine dinucleotide, a co-factor of the D-amino acid oxidase; (5) peroxidase; (6) ortho-dianisidine; and (7) D-amino acid oxidase. The Penzym ® assay suffers several disadvantages which make it less than acceptable to dairy farmers and milk haulers. Among the most significant disadvantages is the requirement for handling an excessive number of separately packaged aqueous reagents.

Many researchers have suggested impregnating paper and other materials with reagents which can be conveniently used for "dip-and-read" tests. For example, Johnson et al, U.S. Pat. No. 4,046,514, September 6, 1977, teach impregnating fibers with reagents and thereafter forming the fibers into a carrier matrix. The examples include a self-calibrated glucose test incorporating glucose oxidase in cotton fibers which are woven into the test strip. Bauer, U.S. Pat. No. 4,390,621, June 28, 1983, suggests impregnating filter paper with glucose oxidase and peroxidase. Lange et al, U.S. Pat. No. 3,802,842, April 9, 1974, suggest covering a filter paper test strip impregnated with reagents for detection of glucose, including glucose oxidase and peroxidase, with a fine fabric meshwork including polyester fabric and nylon fabric.

Enzymes are well known for their lack of predictability in terms of stability. Thus, while glucose oxidase and peroxidase retain their activity when dried on cellulosic-based materials D-amino acid oxidase has been found to lose its activity when dried on cellulosic materials.

SUMMARY OF THE INVENTION

Applicants have found that D-amino acid oxidase can be coated and dried of a variety of synthetic fibers without appreciable loss of activity. In one aspect the present invention is a stable enzyme formulation comprised of a non-cellulosic fabric having coated and dried thereon D-amino acid oxidase.

In another aspect of the invention, the D-amino acid oxidase is coated and dried on woven, nonwoven, or knit fabrics made from polyolefin, nylon, polyester, or polyurethane fibers.

Yet another aspect of the invention involves coating the D-amino acid oxidase on a polyolefin fabric which has been pretreated with a surfactant to increase wettability, the preferred surfactant being Aerosol OT (American Cyanamide Company, Wayne, N.J.).

The D-amino acid oxidase also can be successfully coated and dried on both woven and nonwoven webs. Use of a blown microfibrous web comprised of microfiber filaments having an average fiber diameter of up to 10 microns and length of at least 60 cm is preferred. The most preferred embodiments entail use of polybutylene or polypropylene blown microfibrous webs which have been pretreated with surfactant.

The activity of D-amino acid oxidase coated and dried on a noncellulosic fabric is not adversely affected when the fabric is also coated with analytically effective amounts of reagents used to detect beta-lactam antibiotics. Thus kits to test for beta lactam antibiotics can now be prepared using the present invention. More specifically, in addition to coating the fabric with D-amino acid oxidase, the fabric may be coated with one or more of the reagents for the assay including peroxidase, flavin adenine dinucleotide, a peroxide sensitive dye, and a D,D-carboxypeptidase substrate containing a carboxyterminal D-alanine. To complete the kit D,D-carboxypeptidase R39 enzyme is provided separately in either aqueous form or dried on a separate piece of fabric.

If desired, and if proper conditions are used during the preparation, all of the reagents necessary to detect the presence of a beta-lactam antibiotic can be coated on a single fabric support. In this embodiment of the invention the fabric has coated on it D-amino acid oxidase, D,D-carboxypeptidase, peroxidase, flavin adenine dinucleotide, a peroxide sensitive dye, and a D,D-carboxypeptidase substrate containing a carboxyterminal D-alanine.

In both the kit containing the D,D-carboxypeptidase enzyme on the fabric and the kit wherein the D,D-carboxypeptidase enzyme is supplied separately, the preferred peroxide sensitive dye is dicarboxidine or ortho-dianisidine. The preferred D,D-carboxypeptidase substrate is N,N-diacetyl-L-lysyl-D-alanyl-D-alanine.

Thus, in the most preferred embodiment the D-amino acid oxidase is coated on a microfibrous web of a polyolefin, e.g., polypropylene or polybutylene, together with peroxidase, flavin adenine dinucleotide, ortho-dianisidine dye, and N,N-diacetyl-L-lysyl-D-alanyl-D-alanine.

DETAILED DESCRIPTION

The present invention is useful in any assay employing D-amino acid oxidase wherein dry storage and extended shelf life are desired. The preferred use of the invention is in the context of testing dairy products for beta-lactam antibiotics (penicillins and cephalosporins). Accordingly the description of the invention will be in the context of preparation of a rapid assay suitable for use by the dairy farmer and milk hauler.

The preferred beta-lactam antibiotic assay is described copending application Ser. No. 661,661. That assay comprises the steps of: (1) forming a reaction medium by adding a liquid sample (e.g., raw milk) to a predetermined amount of a combination of dry reagents comprising D,D-carboxypeptidase, a substrate for D,D-carboxypeptidase containing a carboxyterminal D-alanine, and a reagent system which produces a color reaction in the presence of D-alanine; (2) incubating the reaction medium at a temperature between about 20° to 60° C for a predetermined period of time; (3) adding a material which quenches the color-producing reaction; and (4) examining the color of the reaction medium. In the present invention, the D-amino acid oxidase forms a part of the color-producing reagent system. That system further includes a cofactor for D-amino acid oxidase, peroxidase, and an organic redox indicator, e.g., ortho-dianisidine, which undergoes a color change when oxidized.

In order for the foregoing assay to detect specific minimum amounts of beta-lactam antiiotics, a minimum amount of D,D-carboxypeptidase enzyme must be used. To detect a concentration greater than $5 \times 10^{-8}$ moles/liter of a beta-lactam antibiotic such as Penicillin G in a test sample to which all of the assay reagents are added simultaneously, at least about $2 \times 10^{-8}$ moles/liter of enzyme are required. The preferred D,D-carboxypeptidase enzyme is that produced by Actinomadura-R39. Other streptomyces D,D-carboxypeptidase enzymes are known to be reversibly inhibited by beta-lactam antibiotics, but the R39 enzyme is preferred because its rate of inactivation is very rapid and the reversal of inhibition is very slow. Thus, over short periods of time, exposure of R39 enzyme to beta-lactam antibiotic results in a stoichiometric loss of R39 catalytic activity. The preferred R39 enzyme is available from UCB Biochemicals, Brussels, Belgium. It is a water-soluble protein having a molecular weight of about 53,000.

The substrate for the carboxypeptidase may be any peptide whose structure includes a carboxyterminal D-alanine. Examples of suitable substrates are described by Ghuysen et al., Ann. Rev. Biochem., 48, p. 73–101 (1979). A preferred substrate is N,N-diacetyl-L-lysyl-D-alanyl-D-alanine. Especially preferred is the monoacetyl tripeptide which is hydrolyzed at nearly twice the rate of the diacetyl tripeptide.

The D-amino acid oxidase forms a part of the reagent system which produces a color change in the presence of D-alanine. D-amino acid oxidase, in the presence of a cofactor, flavin adenine dinucleotide, oxidatively deaminates D-alanine to produce pyruvate, ammonia and hydrogen peroxide. The D-amino acid oxidase and its cofactor, flavin adenine dinucleotide, are available commercially from Sigma Chemical Company.

The color-forming reagent system also includes a colorless precursor which is oxidized by the peroxide generated from D-alanine. Suitable precursor dyes include dicarboxidine, (gamma, gamma-4,4'-diamino-3,3'-(biphenylenedioxy)dibutyric acid), ortho-dianisidine, 4-amino antipyrrole plus phenol, ortho-phenylenediamine, toluidine and the like. Dicarboxidine (Kabi vitrum, Stockholm, Sweden) and ortho-dianisidine (Sigma Chemical Co ) are the preferred dyes. The enzyme peroxidase catalyzes formation of the colored species. Peroxidase, e.g., horseradish peroxidase, is commercially available from sources such as Sigma Chemical Company.

A wide variety of fibers may be used to form the fabric which serves as a reagent carrier system in the present invention. Good success has been achieved using fabrics made from polyolefins such as polyethylene, polypropylene, and polybutylene; polyamides such as the various nylons; polyesters such as poly(ethylene terephthalate); and polyurethanes such as polyether polyurethanes. Similar success should occur with use of polyvinyl chlorides, polystyrenes, and polysulfones. Additionally fibers of co-extruded polymers such as polyester and polyolefins should be suitable. Further, copolymers of any of the foregoing should prove acceptable.

Satisfactory results have been obtained with both woven and nonwoven fabrics. Applicants would expect acceptable results with a knit fabric. Nonwoven fabrics are preferred, and nonwoven microfibrous webs wherein the filaments have an average fiber diameter of up to 10 microns and a length of at least 60 cm are especially preferred. Webs of this type are readily available commercially and the methods of making them are well known. U.S. Pat. No. 3,978,185 to R. A. Wente et al. describes one such method. Nonwoven microfibrous webs are preferred because of their ease of manufacture, lower material cost, allowance for variation in fiber texture and fiber density, and greater surface area for carrying of more reagents.

Where the fabric is made from a hydrophobic polymer such as polypropylene or polybutylene, pretreatment of the fabric with a surfactant is recommended. Although satisfactory results have been obtained with fabrics made from polyamides that have not been surfactant treated, use of a surfactant facilitates wetting of the fabric thereby allowing the reagents applied to the fabric to be spread and distributed through its surface. The surfactant may be cationic, anionic, or nonionic. The surfactant must be nonreactive with the reagent system coated on the fabric. Suitable surfactants include Emersal 6434 (anionic) (Emery Industries); Triton X-200 (cationic) (Rohm & Haas, Philadelphia, Pa.), Triton X-100 (nonionic) (Rohm & Haas, Philadelphia, Pa.,), Miranol-2CM (Miranol Chemical Company, Dayton, N.J.), and Aerosol OT (American Cyanamide Co., Wayne, N.J.). The preferred surfactant is Aerosol OT.

A variety of methods can be used to coat the fabric with the reagent system. Coating may be effected in a batch process, for example, by immersing the fabric in a solution containing the reagents to be coated, or in a continuous process, for example, by spraying the reagent solution on a moving belt of fabric. The fabric may be precut or cut after coating. The reagents may be applied from a single solution, or they may be applied with multiple solutions containing one or more reagents. The only requirement is the deposition of an analytically effective amount of reagents.

Where the D,D-carboxypeptidase and its substrate are both to be coated on fabric, reaction of the enzyme with the substrate should be avoided. This requires careful handling of the reagents to avoid reaction and deactivation of the enzyme. In the recommended procedure, all reagents except D,D-carboxypeptidase are coated on the web which is then lyophilized. Thereafter, the D,D-carboxypeptidase is added, preferably to the back side of the web relative to the other reagents, and the web cooled as rapidly as possible to −40° C. or colder for lyophilization.

As mentioned above, the D,D-carboxypeptidase must be present in amounts of at least about $2 \times 10^{-8}$ moles/liter in order to detect concentration greater than about $5 \times 10^{-8}$ moles/liter of a beta lactam antibiotic such as Penicillin G. Coating the fabric with 5 to 10 microliters a solution containing at least about $2 \times 10^{-7}$ moles/liter of D,D-carboxypeptidase has been found sufficient to achieve deposition of an amount sufficient to detect antibiotic contamination in concentrations greater than $5 \times 10^{-8}$ moles/liter on a piece of the preferred microfibrous web fabric having a surface area of about 1/32 square inch.

The remaining reagents are preferably provided in excess. Large excesses should be avoided, however, because the reagents are expensive and very large excesses may have a negative effect on the assay. Coating of a fabric sample of the preferred microfibrous web having a surface area of about 1/16 square inch with a solution buffered to a pH range of 7.7 to 8.3 and containing reagents in the following minimum concentrations should result in deposition of an analytically effective amount of reagent.

| Reagents | Concentrations |
|---|---|
| D-amino acid oxidase | 0.2 mg/ml |
| flavin adenine dinucleotide | 0.01 mg/ml |
| peroxidase | 0.01 mg/ml |
| N,N—diacetyl-L-lysyl-D-alanine | 2.0 mg/ml |
| dicarboxidine | 0.5 mg/ml |
| ortho-dianisidine | 0.5 mg/ml |

The reagents can be conveniently coated on a fabric example of the preferred microfibrous web having a surface area of about 1/16 square inch by spraying the fabric with a single solution buffered to a pH range of 7.7 to 8.3 and containing the reagents in following concentration ranges.

| Reagents | Concentrations |
|---|---|
| D-amino acid oxidase | 0.20 to 2.0 mg/ml |
| flavin adenine dinucleotide | 0.01 to 0.2 mg/ml |
| peroxidase | 0.01 to 2.0 mg/ml |
| N,N—diacetyl-L-lysyl-D-alanine | 2.0 to 20 mg/ml |
| dicarboxidine | 0.5 to 10 mg/ml |
| ortho-dianisidine | 0.5 to 10 mg/ml |

Applicants prefer to coat fabric samples of polybutylene or polypropylene microfibrous webs having filaments with an average diameter of up to 10 microns, length of at least 60 cm and surface area of about 1/16 square inch by spraying a single solution which is buffered with HEPES buffer (pH 7.8 made from 0.1M N-(2-hydroxy ethyl)piperzaine-N'(2-ethanesulfonic acid), 0.2 M NaCl, and 0.05 M $MgCl_2$) and contains all the reagents in the concentrations shown below.

| Reagents | Concentrations |
|---|---|
| D-amino acid oxidase | 1.0 mg/ml |
| Flavin adenine dinucleutide | 0.15 mg/ml |
| peroxidase | 0.05 mg/ml |
| N,N—diacetyl-L-lysyl-D-alanyl-D-alanine | 20 mg/ml |
| dicarboxidane | 5.0 mg/ml |
| ortho-dianisidene | 5.0 mg/ml |

After the fabric has been coated with the reagents, drying may be effected by any convenient process. Good success has been achieved with both air drying and lyophilization. Similarly, alternative methods of separation such as evaporation in vacuo can be used. Caution should be exercised to prevent the temperature of the coated fabric from exceeding 25° C.

The formulations thus obtained are stable at ambient conditions for up to two weeks. If stability of weeks or months is desired, the formulations should be protected from atmospheric moisture and heat. Preferably the formulation is separated into a dry atmosphere and packaged with a moisture-impervious foil, plastic, or paper. Most preferably the formulation is packaged in a moisture impervious container and refrigerated. When protected in this manner the formulation will retain stability and provide a reliable test for at least 9 months.

When provided with the formulation prepared as described above, the end user needs to supply a device to maintain constant temperature for the incubation period, such as an oven, electric crockpot, or preferably a small incubator. To perform a test, the user need only mix the test sample (e.g. 50 microliters) with the test reagents and incubate for a set period, e.g. 5 minutes. Incubation may be at any temperature between about 20° C and 60° C. Incubating in a temperature range between about 45° C and 50° C is preferred. Where the D,D-carboxypeptidase is added separately from the remaining reagents, the incubation period should begin with addition of the D,D-carboxypeptidase. The color forming reaction can be stopped at the end of the incubation period by reducing the pH to about pH 4.0 or lower. Strong inorganic acids such as sulfuric, hydrochloric, phosphoric, and the like are conveniently used to lower the pH. If dicarboxidine or ortho-dianisidine is used as the dye, the addition of sulfuric acid to provide a final concentration of about 25% by volume provides an enhancement of color in addition to stopping the reaction. Alternatively, an acid provided in tablet form with a kit containing the reagent formulations may be desired. For this purpose an acid such as sulphamic acid or $H_3ASO_4$ maybe used.

After the color forming reaction has been quenched by lowering the pH, the color intensity can be read and correlated to known concentrations of beta-lactam antibiotic. Where accurate quantitative results are desired, sophisicated equipment such as spectrophotometers may be used to read the color intensity. This intensity can then be compared to intensities obtained with samples having known amounts of antibiotic. For more qualitative field determinations, the test sample can be compared to a calibrated color chart provided with the test kit.

The invention may be further illustrated by the following non-limiting examples.

Example 1

Twenty samples of microfibrous web (propylene treated with about one percent f surfactant (Aerosol OT, American Cyanamid Co., Wayne, N. J.), each sample measuring ¼ inch by ¼ inch and weighing about 3.5 to 4.0 mg, were saturated with 10 microliters of a solution made by mixing 0.10 ml of HEPES buffer (pH 7.8 made from 0.1M N-(2-hydroxyethyl)piperazine-N'-(2-ethanesulfonic acid) 0.2M sodium chloride and 0.05M magnesium chloride) with 0.220 ml of aqueous flavin adenine dinucleotide solution (0.3 mg/ml.); 0.170 ml of D-amino acid oxidase solution 5 mg/ml in 3.2M aqueous ammonium sulfate); 0.010 ml of horseradish peroxidase solution (9 mg/ml horseradish peroxidase in 3.2M aqueous ammonium sulfate), and 0.080 milliliters of distilled water.

Ten of the squares were air-dried in a glass Petri dish covered with aluminum foil for one hour. These squares were then placed in individual tubes which were stoppered, and then placed in a desiccator which was refrigerated.

Ten of the squares were lyophilized in a covered glass Petri dish for seven hours at −25° to +5° C. These squares were then placed in individual tubes which were stoppered, and then placed in a desiccator which was refrigerated.

EXAMPLE 2

Using squares from Example 1, two each of air-dried squares and lyophilized squares were tested for their ability to assay for D-alanine in milk. The presence of D-alanine shows the absence of beta-lactam antibiotic according to the assay. Tubes containing none (control), untreated squares (blank) and either air-dried or lyophilized test squares were prepared. The control, blank and test square tubs each contained 50 microliters of milk plus 10 microliters of an aqueous solution of a D,D-carboxypeptidase (concentration 1.01 mg/ml.). Each sample was incubated at 47° C. for 5 minutes, then 10 microliters of ortho-diasnisidine dye was added. To the control and blank was added 30 microliters of the solution used to prepared the squares of Example 1. To each of the tubes was added 10 microliters of aqueous N,N-diacetyl-L-lysyl-D-alanyl-D-alanine (20 mg/ml) to begin the assay. Each of the six samples was then incubated at 47° C. for 15 minutes. The reactions were terminated by adding an equal volume of 50% sulfuric acid. Approximately equivalent pink colors developed in all samples.

EXAMPLE 3

After sitting eight days in the refirgerated desiccator two each of air-dried squares and lyophilized squares from Example 1 were tested for their ability to assay for D-alanine in milk using the method of Example 2. All of the squares assayed gave excellent pink colors.

EXAMPLE 4

Two solutions were prepared as described below. Reagents obtained from UCB Biochemicals, Brussels, Belgium were used. Mixture (A) contained 0.110 ml of flavin adenine dinucleotide (0.3 mg/ml in water), 0.085 ml of D-amino acid oxidase (5 mg/ml in 3.2M ammonium sulfate); 0.005 ml of peroxidase (9 mg/ml in 3.2M ammonium sulfate); 0.113 ml of HEPES buffer and 0.063 ml of N,N,diacetyl-L-lysyl-D-alanyl-D-alanine (37.5 mg/ml).

A second solution (B) was a mixture of 0.110 ml of flavin adenine dinucleotide (0.3 mg/ml in water); 0.085 ml of D-amino acid oxidase (5 mg/ml in 3.2M ammonium sulfate); 0.005 ml of peroxidase 9 mg/ml in 3.2M ammonium sulfate); 0.050 ml of HEPES buffer; 0.063 ml of N,N-diacetyl-L-lysyl-D-alanyl-D-alanine (37.5 mg/ml) solution and 0.063 ml of ortho-dianisidine (20 mg/ml) solution.

Twenty samples of web each measuring ¼ inch square similar to those of Example 1 were each saturated with 15 microliters of solution (A). Another twenty squares were saturated with solution (B).

Ten squares saturated with solution (A) and ten squares saturated with solution (B) were air-dried for three hours.

Ten squares saturated with solution (A) and ten squares saturated with solution (B) were lyophilized for 3.5 hours.

Solution blanks were run on (A) and (B) by adding to 15 microliters of solution, 50 microliters of milk, 10 microliters of D,D-carboxypeptidase enzyme solution and in the case of solution A only 10 microliters of ortho-dianisidine solution.

Solution controls consisted of 50 microliters of milk and 10 microliters of D,D-carboxypeptidase to which were added either 15 microliters of solution (A) and 10 microliters of ortho-dianisidine solution (5.0 mg/ml) or 15 microliters of solution (B).

Tests on solution controls and all squares were carried out by incubating at 47° C for 15 minutes then quenching with 50% aqueous sulfuric acid. Every square showed excellent pink color comparable to the solution controls.

EXAMPLE 5

Samples of fibrous web (of about 1/4 inch square) were soaked in 10 microliters of 0.1% (W/Y) solution of Aerosol OT surfactant, then allowed to dry. The web samples were of varying thickness and were prepared to provide squares which would absorb 15 to 20 microliters of solution. Each web sample was treated with 10 microliters of a solution of the following composition:

| Ingredient | Amount |
| --- | --- |
| D-amino acid oxidase (5 mg/ml) | 0.20 ml |
| horseradish peroxidase (9.0 gm/ml) | 0.05 ml |
| flavin adenine dinucleotide (1 mg/ml) | 0.10 ml |
| dicarboxidine (5 mg/ml) | 0.20 ml |
| HEPES buffer | 0.45 ml |
| water | 0.50 ml |

After 24 to 36 hours of drying, the activity was measured by adding the web to 0.620 ml of an assay solution containing 0.1M D-alanine, 0.2 ml; 1.0 mg/ml flavin adenine dinucleotide, 0.1 ml; 5.0 mg/ml dicarboxidine, 0.05 ml; 6.6 mg/ml peroxidase in 3.2M ammonium sulfate, 0.025 ml; HEPES Buffer, 0.60 ml.

The assay solution plus web were incubated with continuous shaking in a water bath at 30° C. At timed intervals 200 microliter samples were withdrawn and added to 200 microliters of 50% sulfuric acid (v/v) to stop the reaction. The color that developed was read using microcuvettes, 1 cm path length, in a Beckman DU-8 spectrophotometer at a wavelength of 540 nM. The D-amino acid oxidase activity is proportional to the rate of increase in absorbance at 540 nM of the assay samples. The slopes, $A_{540/min}$, of the least squares regression lines fitted to the assay data was used to compare the activity of the preparations. The results are shown in the following Table I.

TABLE I

| Material | Enzymatic Activity ($A_{540/min}$) | % of Enzyme Solution Enzymatic Activity |
|---|---|---|
| Enzyme | 0.1213 | 100 |
| Polybutylene | 0.1098 | 90.5 |
| Polypropylene | 0.0358 | 29.5 |
|  | 0.0441 | 36.3 |
| Polyethylene Terephthalate | 0.1085 | 89.4 |
| Polyamide | 0.1010 | 83.3 |
| Polyamide | 0.1013 | 79.9 |
| Polyamide Without Surfactant | 0.0969 | 79.9 |
|  | 0.0736 | 60.6 |

EXAMPLE 6

Samples of woven fabric, each sample ½ inch square, were saturated with 10 microliters of a solution made by mixing 0.45 ml of HEPES buffer with 0.10 ml of flavin adenine dinucleotide solution (1.3 mg/ml. in water); 0.20 ml of D-amino acid oxidase solution (5 mg/ml in 3.2M aqueous ammonium sulfate); 0.050 ml of horseradish peroxidase solution (9 mg/ml horseradish peroxidase in 3.2M aqueous ammonium sulfate), 0.20 ml of dicarboxidine (5 mg/ml in water) and 50 microliters of distilled water.

Each of the squares was placed in a plastic Petri dish covered with aluminum foil and air dried for about 6 hours. The dishes were placed in a desiccator which was refrigerated.

The woven fabrics used were:
(1) 70 den nyl 6012/90 (commercially available from Burlington Industries) (pretreated with 10 microliters of 0.1% W/v Triton X100 and dried to increase its wettability).
(2) polyester taffeta—50 den poly/150 den poly 2100/64 (commercially available from Burlington Industries).
(3) 150 bright cellulose acetate warp with 150/opaque cellulose acetate (commercially available from Burlington Industries).
(4) 30 den warp and fill nylon 443/682 (commercially available from Milliken).

EXAMPLE 7

The D-amino-acid oxidase activity of the enzyme-saturated woven fabric samples of Example 6 was measured after 8 days of drying. The activity was measured by adding the fabric sample to 0.800 ml of an assay solution containing 0.1M D-alanine, 0.2 ml; 1.0 mg/ml flavin adenine dinucleotide, 0.1 ml; 5.0 mg/ml dicarboxidine, 0.05 ml; 6.6 mg/ml peroxidase in 3.2M ammonium sulfate, 0.075 ml; HEPES buffer, 0.60 ml. The activity was compared to assay solution without fabric.

The assay solutions plus woven fabric sample were incubated with continuous shaking in a water bath at 30° C. At timed intervals 200 microliter samples were withdrawn and added to 200 microliters of 50% sulfuric acid (v/v) to stop the reaction. The color which developed was read using microcuvettes, 1 cm path length, in a Beckman DU-8 spectrophotometer at a wavelength of 540 nanometers. The D-amino acid oxidase activity is proportional to the rate of increase in absorbance at 540 nM of the assay samples. The slopes, $A_{540/min}$, of the least squares regression lines fitted to the assay data were used to compare the activity of the preparations. Only fabric sample 3, which is cellulose acetate-based lost significant amounts of activity.

EXAMPLE 8

Microfibrous web samples (polypropylene treated with about 1% of Aerosol OT ®, American Cyanamid Co., Wayne, N.J.), each sample measuring ¼ inch by ⅛ inch and weighing about 3.5 to 4.0 mg, were saturated with enzyme and buffer obtained from a commercially available Penzym ® kit (UCB Biochemicals, Brussels, Belgium). Each of five samples of web were saturated with 5 microliters of a solution prepared by reconstituting a vial from the Penzym ® kit containing D,D-carboxypeptidase and HEPES buffer with 500 microliters of water. The moist webs were lyophilized to dryness and stored desiccated at 4° C.

Six squares of web each measuring ¼ inch square were then saturated with 5 microliters of a solution prepared by reconstituting a vial from the Penzym ® kit containing N,N-diacetyl-L-lysyl- D-alanyl-D-alanine and ortho-dianisidine with 500 microliters of water and 10 microliters of a suspension from a Penzym ® vial containing D-amino acid oxidase, peroxidase and flavin adenine dinucleotide. The moist webs were lyophilized and stored desiccated at 4° C.

Solutions of Penicillin G in whole milk at concentrations of 0.1; 0.05; 0.03 and 0.01 units of Penicillin G per milliliter were prepared, and tested. All tests were run by reacting for fifteen minutes at 50° C, then measuring the color obtained.

A blank assay was run with 50 microliters of pure milk plus a web containing dry D,D-carboxypeptidase and HEPES buffer and a web containing all of the other essential components of the assay. A dark pink color was obtained indicating the presence of D-alanine and the absence of any beta-lactam antibiotic.

A blank assay was run with 50 microliters of pure milk plus a web containing all of the essential components of the assay except D,D-carboxypeptidase. No color developed (as expected) since an essential component of the assay was missing.

A group of assays was run using each of the milk solutions of Penicillin G prepared above. Fifty microliters of each milk solution was reacted with the pairs of webs containing all of the essential components of the assay. Pink colors were obtained for concentrations of Penicillin G of 0.01 and 0.03 Units per milliliter. No color was obtained at concentrations of Penicillin G of 0.05 and 0.10 units per milliliter, indicating the presence of Penicillin G.

What is claimed is:
1. A stable enzyme formulation comprised of a noncellulosic fibrous carrier having coated and dried thereon D-amino acid oxidase, wherein said enzyme is substantially solubilized when said formulation is rehydrated.

2. The formulation of claim 1 wherein the non-cellulosic fibrous carrier is selected from a group consisting of polyolefins, nylons, polyesters, and polyurethanes.

3. The formulation of claim 1 wherein the fibrous carrier is a nonwoven fibrous web.

4. The formulation of claim 2 wherein the fibrous carrier is a non-woven web.

5. The formulation of claim 1 wherein the fibrous carrier is a blown microfibrous web.

6. The formulation of claim 2 wherein the fibrous carrier is a blown microfibrous web.

7. The formulation of claim 2 wherein the fibrous carrier is a polybutylene blown microfibrous web and has been pretreated with surfactant.

8. The formulation of claim 2 wherein the fibrous carrier is a polypropylene blown microfibrous web and has been pretreated with surfactant.

9. A stable enzyme formulation prepared by coating and drying D-amino acid oxidase on a non-cellulosic fibrous carrier, wherein said enzyme is substantially solubilized when said formulation is rehydrated.

* * * * *